United States Patent
Norcini et al.

(10) Patent No.: US 10,017,435 B2
(45) Date of Patent: Jul. 10, 2018

(54) PROCESS FOR THE PREPARATION OF A PHENYLINDAN COMPOUND

(71) Applicant: IGM RESINS ITALIA S.R.L., Milan (IT)

(72) Inventors: Gabriele Norcini, Comabbio (IT); Angelo Casiraghi, Milan (IT); Enzo Meneguzzo, Sesto Calende (IT); Giovanni Floridi, Novara (IT); Giuseppe Li Bassi, Gavirate (IT)

(73) Assignee: IGH RESINS ITALIA S.R.L., Milan ( * ) Notice: Subject to any disclaimer, the term of this patent is extended or adjusted under 35 U.S.C. 154(b) by 56 days.

(21) Appl. No.: 15/316,296

(22) PCT Filed: Jun. 8, 2015

(86) PCT No.: PCT/EP2015/062665
§ 371 (c)(1),
(2) Date: Dec. 5, 2016

(87) PCT Pub. No.: WO2015/189125
PCT Pub. Date: Dec. 17, 2015

(65) Prior Publication Data
US 2018/0141882 A1    May 24, 2018

(30) Foreign Application Priority Data
Jun. 10, 2014   (IT) .............. VA2014A0019

(51) Int. Cl.
| | | |
|---|---|---|
| C07C 2/64 | (2006.01) |
| C07C 2/72 | (2006.01) |
| C07C 45/72 | (2006.01) |
| C07C 45/46 | (2006.01) |
| C07C 45/63 | (2006.01) |
| C07C 45/64 | (2006.01) |
| C07C 13/465 | (2006.01) |
| C07C 22/04 | (2006.01) |
| C07C 45/42 | (2006.01) |
| C07C 45/65 | (2006.01) |
| C07C 45/81 | (2006.01) |
| C07C 49/788 | (2006.01) |
| C07C 49/792 | (2006.01) |
| C07C 49/794 | (2006.01) |
| C07C 49/82 | (2006.01) |
| C07C 17/14 | (2006.01) |

(52) U.S. Cl.
CPC ............ *C07C 13/465* (2013.01); *C07C 17/14* (2013.01); *C07C 22/04* (2013.01); *C07C 45/42* (2013.01); *C07C 45/46* (2013.01); *C07C 45/63* (2013.01); *C07C 45/64* (2013.01); *C07C 45/65* (2013.01); *C07C 45/72* (2013.01); *C07C 45/81* (2013.01); *C07C 49/788* (2013.01); *C07C 49/792* (2013.01); *C07C 49/794* (2013.01); *C07C 49/82* (2013.01); *C07C 2523/04* (2013.01)

(58) Field of Classification Search
CPC .. C07C 2/64; C07C 2/72; C07C 45/72; C07C 45/46; C07C 45/63; C07C 45/64; B01J 31/10
USPC .................. 585/469, 319, 320, 321; 568/316
See application file for complete search history.

(56) References Cited

U.S. PATENT DOCUMENTS

| | | | |
|---|---|---|---|
| 4,987,159 A | 1/1991 | Li Bassi et al. |
| 2007/0168144 A1 | 7/2007 | Demizu et al. |
| 2009/0018354 A1 | 1/2009 | End et al. |

FOREIGN PATENT DOCUMENTS

| | | |
|---|---|---|
| CN | 102603509 A | 7/2012 |
| EP | 161463 | 11/1985 |
| EP | 1389177 B1 | 10/2008 |
| EP | 1620382 B1 | 9/2013 |
| WO | 2004099111 | 11/2004 |

OTHER PUBLICATIONS

Song, Guo-Qiang et al. "Preparation and Properties of Difunctional Hydroxy Ketone as Photoinitiator", vol. 30, No. 8, Aug. 2013 (Aug. 2013), pp. 888-891.
Written Opinion of the International Searching Authority of International Parent Application No. PCT/EP2015/062665 dated Aug. 19, 2015.
International Search Report of International Parent Application No. PCT/EP2015/062665 dated Aug. 19, 2015.
Search Report of Italian Priority Application No. ITVA20140019 dated Jan. 25, 2015.

*Primary Examiner* — Thuan D Dang

(57) ABSTRACT

The present invention refers to a process for producing 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) that comprises the synthesis from cumene and dimerization of 2-methyl-1-(4-(prop-1-en-2-yl)phenyl)propan-1-one in the presence of acid catalysts.

11 Claims, No Drawings

PROCESS FOR THE PREPARATION OF A PHENYLINDAN COMPOUND

RELATED APPLICATIONS

This application is the US national phase application of international application number PCT/EP2015/062665, filed 8 Jun. 2015, which designates the US and claims priority to Italian Application No. VA2014A000019 filed 10 Jun. 2014, the contents of each of which are hereby incorporated by reference as if set forth in their entireties.

TECHNICAL FIELD

The present invention refers to a process for producing a regioisomer of a phenylindan photoinitiator (5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene, dimer isomer 5), in solid and pure form.

BACKGROUND OF THE ART

The use of oligomeric photoinitiators in photopolymerisation has several advantages in comparison with the use of monomeric photoinitiators, such as lower migratability of the photoinitiator and reduced amount of volatile compounds derived from their photodecomposition. Those characteristics are important for the industrial use because they reduce the risk of contamination of the finished products.

Among the known oligomeric photoinitiators, the alpha-hydroxycarbonyl derivatives of oligomers of alpha-methylstyrene of formula A, wherein n is a number equal or greater than zero, are mostly appreciated in the field.

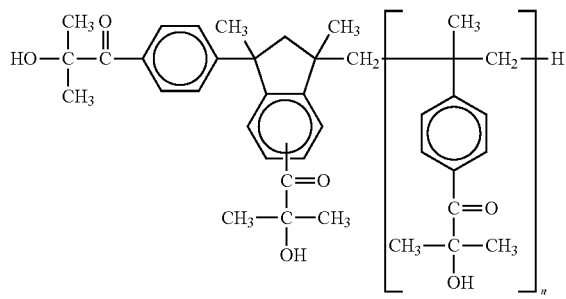

A

These photoinitiators are described in U.S. Pat. No. 4,987,159 and they are mainly constituted by mixtures of dimer and trimer isomers. At room temperature these mixtures of dimer and trimer isomers are highly viscous products that usually require pre-heating for easy handling.

As a consequence, solid mixtures of alpha hydroxycarbonyl derivatives of alpha-methylstyrene oligomers in powder form have been developed and are now highly appreciated photoinitators for photopolymerising acrylic systems.

Their composition and synthesis is reported in EP 1389177.

The solid mixtures of alpha hydroxycarbonyl derivatives of alpha-methylstyrene oligomers of EP 1389177 contain about 90-98% of two dimer isomers: 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) and 6-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 6).

Dimer isomer 5 is the compound of formula V:

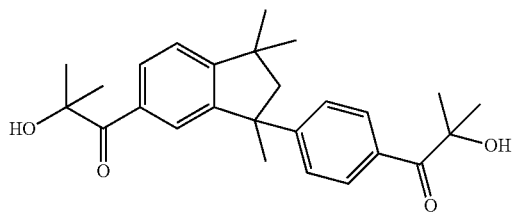

V

Dimer isomer 6 is the compound of formula VI

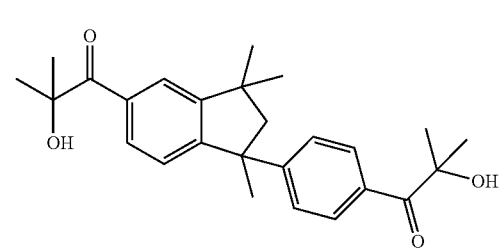

VI

The process of EP 1389177 provides these solid mixtures through controlled crystallization of the high viscosity mixtures of alpha-hydroxycarbonyl derivatives of oligomers of alpha-methylstyrene, whose synthesis is described, for instance, in U.S. Pat. No. 4,987,159.

Both dimer isomers are active as photoinitiators, but dimer isomer 5 is more reactive in photopolymerization than dimer isomer 6, as it is also reported in EP 1389177.

One of the advantage of the controlled crystallization of EP 1389177 is that it provides solid mixtures of alpha hydroxycarbonyl derivatives of alpha-methylstyrene oligomers that are enriched in dimer isomer 5.

A process for the preparation of a crystalline mixture of dimer isomer V and VI is also described in EP 1620382. The process uses 1,1,3-trimethyl-1-phenylindan as the starting product and may be adapted for the preparation of the individual dimer isomer V through separation of one of the intermediates.

Both the process of EP 1389177 and the process of EP 1620382 prepare alpha-hydroxycarbonyl derivatives of alpha-methylstyrene dimers by acylation of alpha-methylstyrene oligomers or dimers. Due to the fact that acylation occurs both in the 5- and 6-positions, mixtures of 5- and 6-isomers are always obtained and the preparation of dimer isomer 5 in enriched or isolated form implies the discharge or separate use of the less reactive dimer isomer 6.

As a consequence it would be highly desirable to design a short, efficient and isomer 6-free synthesis of dimer isomer 5 which also dispenses with costly and inconvenient purification steps and provides the product in solid and pure form.

It has now been found that this objective is achieved by a process that comprises the synthesis from cumene and dimerization (cyclization) of 2-methyl-1-(4-(prop-1-en-2-yl)phenyl)propan-1-one in the presence of acid catalysts.

SUMMARY OF THE INVENTION

Accordingly, the main object of the present disclosure is a process for the preparation of 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer 5) comprising the following steps:

i. cumene is acylated with a compound of formula Ia, where $X_0$ is Cl or Br to obtain a compound of formula IIa and the compound of formula IIa is halogenated to obtain a compound of formula III, where $X_1$ is Cl or Br; or cumene is halogenated to obtain a compound of formula IIb and the compound of formula IIb is acylated with the compound of formula Ia to obtain the compound of formula III, according to the following scheme:

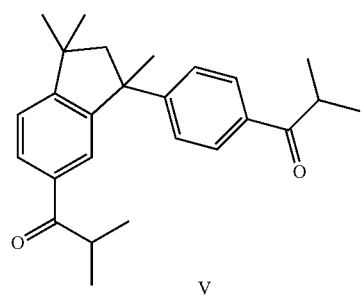

V

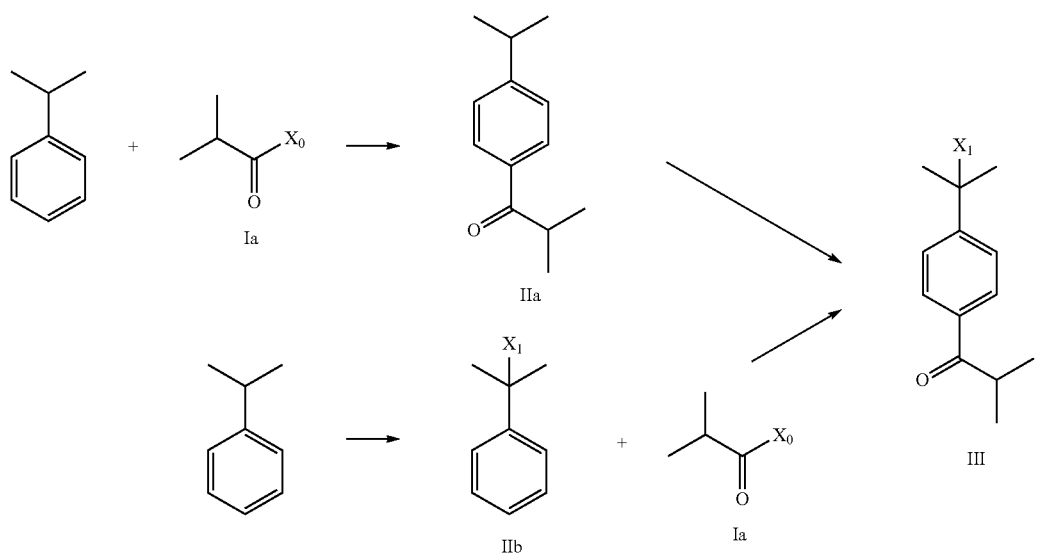

ii. the compound of formula III is dehydrohalogenated with a base to obtain a compound of formula IV and the compound of formula IV is cyclized with an acid catalyst to obtain the compound of formula V, according to the following scheme:

or the compound of formula III is directly cyclized with an acid catalyst to obtain the compound of formula V;

iii. the compound of formula V is halogenated to obtain the compound of formula VI

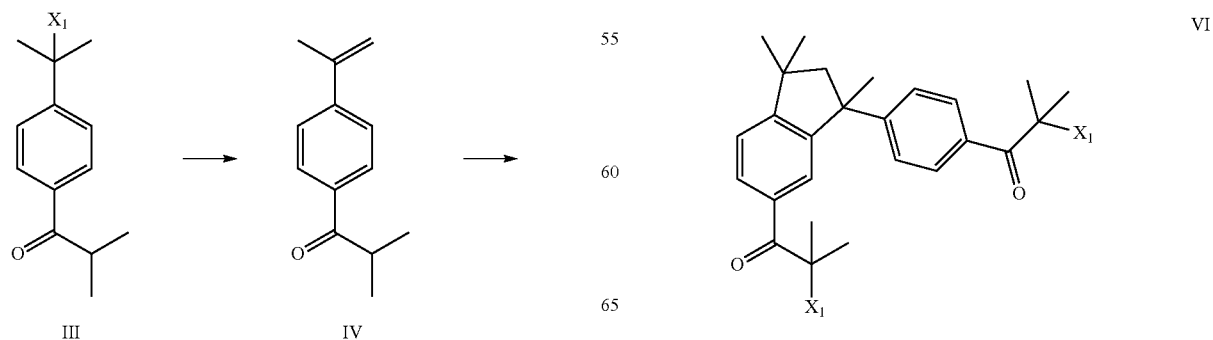

iv. the compound of formula VI is hydrolyzed to obtain the compound of formula VII (dimer isomer 5)

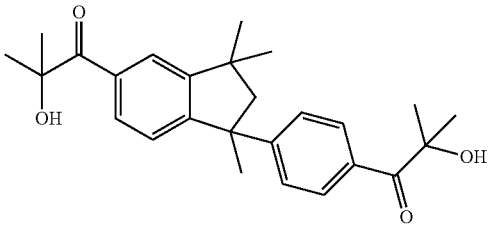

VII

DETAILED DESCRIPTION OF THE INVENTION

The acylation of cumene with a compound of formula Ia is a Friedel Craft acylation. The specific substrate (cumene) renders the acylation highly regioselective, and provides almost exclusively para-substituted cumene derivatives (selectivity about 98% as determined by H-NMR).

Compounds III are therefore easily obtained from cumene in few steps with very high selectivity.

The compounds of formula Ia are commercially available acyl halides. The preferred compound of formula Ia is isobutyryl chloride.

In step i., cumene and the acyl halide are preferably mixed and reacted in the absence of a solvent, or dissolved in an organic solvent. Any solvent which is inert in the acylation conditions may be used. Examples of solvents that can be used are dichloromethane, chlorobenzene, ethylenechloride, 1,2-dichlorobenzene, nitromethane, tetrachlorethane; the preferred solvents are dichloromethane and chlorobenzene.

From 1.50 to 1.10 moles of the acyl halide, preferably from 1.10 to 1.05, per mole of cumene are used.

The acylation of step i. is typically carried out by adding from 1.5 to 0.1 moles per mole of cumene of a Lewis acid, such as $AlCl_3$, $FeCl_3$, $TiCl_4$, $BF_3$ or $SnCl_4$, preferably $AlCl_3$, preferably at temperature between −20° and +20° C., more preferably between −10° and 10° C. The work up of the reaction is made as usual in the art, by hydrolyzing the reaction mixture with water and separating the resulting product, possibly dissolved in the solvent.

Quantitative yields are obtained.

The halogenation of the compound of formula IIa is a benzylic halogenation that can be performed as described in US Pat No 2007/0168114, by reaction of the compound of formula IIa with N-bromosuccinimide with illumination using a sunlight or UV lamp or in presence of catalytic amounts of dibenzoyl peroxide or 2,2'-azoisobutyronitrile (AIBN), or by reaction with chlorine, bromine or sulfuryl chloride, or with t-butyl-ipochlorite under free radical conditions (illumination or presence of catalytic amounts of dibenzoyl peroxide or AIBN). Halogenation may be carried out in the same halogenated solvent that has been used in the acylation of step i., if any, or in another compatible solvent, such as methylene chloride, chloro benzene, 1,2-dichlorobenzene or other halogenated solvent.

Alternatively, in step i. cumene is halogenated in the benzylic position, as reported above for the benzylic halogenations of the compound of formula IIa, to obtain a compound of formula IIb.

The compound of formula IIb is subsequently acylated as described above with the compound of formula Ia, to obtain the compound of formula III.

In step ii. the compound of formula III is dehydrohalogenated with a base, preferably with a strong base such as an alkali metal hydroxide in alcohol, more preferably with NaOH or KOH in alcohol, most preferably with KOH in ethanol, to obtain a compound of formula IV. Typically, from 2 to 1 moles of base are used per mole of compound of formula III and the temperature is kept at 40-100° C., preferably at 60-80° C., during the reaction.

The compound of formula IV is subsequently cyclized with an acid catalyst to obtain the compound of formula V. The acid catalyst can be an inorganic or an organic strong acid or a Lewis acid. The preferred acid catalysts are Lewis acids, clays, ion exchange resins with sulfonic groups in acid form, $C_6$-$C_{18}$ arylsulphonic acids and trifluoromethanesulphonic acid. The most preferred catalysts are Lewis acid, particularly $AlCl_3$, and inorganic acids. The reaction can be carried out in solvents or without solvents at a temperature from 40 to 140° C.

Alternatively or the compound of formula III is directly cyclized with an acid catalyst to obtain the compound of formula V, in the same general conditions reported for the cyclization of compound IV. In this case, the preferred catalyst are ion exchange resins with sulfonic groups in acid form and inorganic acids.

In step iii., the compound of formula V is enol halogenated by using chlorine as reported by way of example in WO 2004/099111, or with bromine or sulfuryl chloride as reported in EP 161463, to give the compound VI.

In step iv. the compound of formula VI is hydrolysed. The compound of formula VI may be reacted with an alkali metal alkoxide, preferably with sodium methylate in methanol and hydrolysed with an aqueous acid to give the compound of formula VII (dimer 5), as reported by way of example in EP 161 463 (Example 2, stages (D') and (E')) and in U.S. Pat. No. 4,987,159 (Example 4); alternatively, the compound of formula VI may be directly hydrolised with an alkali metal hydroxide, by way of example with NaOH 30 wt % in methanol, as described in WO 2004/099111 (Example 1.3), or with NaOH 30 wt % in water, to give the compound of formula VII.

The compound of formula VII may be obtained in solid and pure form by crystallization from toluene, i-propanol, ethyl acetate or other solvent, as reported, by way of example, in EP 1389177.

EXAMPLES

Example 1

1-(4-isopropylphenyl)-2-methylpropan-1-one (compound of formula IIa)

A solution of cumene (38.3 g, 0.315 moles) and i-butyrylchloride (36.0 g, 0.331 moles) in methylene chloride (280 g) was stirred under nitrogen at room temperature. Aluminum chloride (46.0 g, 0.345 moles) was added in portions to the solution in 90 minutes at room temperature. After one additional hour under stirring the solution was poured in iced water under stirring. The organic phase was washed with water and the methylene chloride was distilled off under vacuum. 60.5 g of clear yellow were obtained. Yield: quantitative.

$H_1$NMR (CDCl$_3$, δ ppm): 1.20 (d, 6H), 1.26 (d, 6H), 2.95 (m, 1H), 3.53 (m, 1H), 7.30 (d, 2H), 7.89 (d, 2H).

Example 2

1-(4-(2-chloropropan-2-yl)phenyl)-2-methylpropan-1-one (compound of formula III)

1-(4-isopropylphenyl)-2-methylpropan-1-one (7.61 g, 0.04 moles) was dissolved in chlorobenzene (56 g) and de-oxygenated by nitrogen under stirring at room temperature. Then the solution was cooled at −10° C. and t-butyl hypochlorite (6.55 g, 0.06 moles prepared as described in Organic Syntheses, Coll. Vol. 5, 184 (1973)) was added in one portion obtaining a yellow solution. The stirred solution was illuminated with a 300 W Osram Ultra Vitalux lamp, until the solution was discolored and the temperature raised to 38° C. After cooling to room temperature, the solvent was distilled off under vacuum obtaining 13 g of clear oil. Yield: almost quantitative.

$H_1$NMR (CDCl$_3$, δ ppm): 1.20 (d, 6H), 2.00 (s, 6H), 3.53 (m, 1H), 7.27 (d, 2H), 7.93 (d, 2H).

Example 3

2-methyl-1-(4-(prop-1-en-2-yl)phenyl)propan-1-one (compound of formula IV)

A sample of 1-(4-(2-chloropropan-2-yl)phenyl)-2-methylpropan-1-one (1.05 g, 0.0047 moles) was stirred in a 0.5M solution of KOH in ethanol (10.8 ml, 0.0054 moles). After 1 hour under stirring at 60° C. a precipitate of KCl was observed. The mixture was diluted with methylene chloride (20 ml) and washed with water. The organic phase was dried with sodium sulfate and the solvent distilled off under vacuum affording 0.91 g of clear oil. Yield: 96%

$H_1$NMR (CDCl$_3$, δ ppm): 1.21 (d, 6H), 2.17 (s, 3H), 3.53 (m, 1H), 5.20 (s, 1H), 5.47 (s, 1H), 7.54 (d, 2H), 7.92 (d, 2H).

Example 4

5-(2-methyl-1-oxo-prop-1-yl)-3-(4-(2-methyl-1-oxo-prop-1-yl)phenyl)-2,3-dihydro-1,1,3-trimethyl-1H-indene (compound of formula V)

2-methyl-1-(4-(prop-1-en-2-yl)phenyl)propan-1-one (0.90 g, 0.0048 moles) were dissolved in methylene chloride (15 g) and AlCl$_3$ (1.80 g, 0.0135 moles) was added in two portions in 2 hours at reflux. After an additional hour the reaction was complete (TLC: SiO$_2$ toluene). The mixture was poured in iced water and the organic phase dried over sodium sulfate and the solvent distilled off obtaining 0.80 g of a highly viscous oil. Yield: 89%.

$H_1$NMR (CDCl$_3$, δ ppm): 1.00 (s, 3H), 1.15 (m, 12H), 1.32 (s, 3H), 1.70 (s, 3H), 2.22 (d, 1H), 2.43 (d, 1H), 3.50 (m, 2H), 7.22 (m, 3H), 7.70 (s, 1H), 7.81 (d, 2H), 7.90 (d, 1H).

Example 5

5-(2-chloro-2-methyl-1-oxo-prop-1-yl)-3-(4-(2-chloro-2-methyl-1-oxo-prop-1-yl)phenyl)-2,3-dihydro-1,1,3-trimethyl-1H-indene (compound of formula VI)

1.21 g (0.009 moles) of sulphurylchloride are slowly added to 0.80 g (0.0042 moles) of the compound of formula V in 10 ml of toluene. After two hours at 45° C. the mixture is washed with water, neutralised and the solvent evaporated under vacuum to obtain a viscous oil that solidify after standing. Yield: quantitative.

$H_1$NMR (CDCl$_3$, δ ppm): 1.03 (s, 3H), 1.38 (s, 3H), 1.73 (s, 3H), 1.86 (m, 12H), 2.26 (d, 1H), 2.47 (d, 1H), 7.25 (m, 3H), 7.92 (s, 1H), 8.07 (d, 2H), 8.18 (d, 1H).

Example 6

5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (compound of formula VII, dimer isomer 5)

5-(2-chloro-2-methyl-1-oxo-prop-1-yl)-3-(4-(2-chloro-2-methyl-1-oxo-prop-1-yl)phenyl)-2,3-dihydro-1,1,3-trimethyl-1H-indene (5.2 g, 0.011 moles) was dissolved in methylene chloride (30 g) and a 30% water solution of NaOH (7.30 g, 0.055 moles) were added. The mixture was heated at reflux in presence of tetrabutylammonium bromide (0.10 g). After 8 hours the reaction was complete (TLC SiO$_2$, toluene:ethylacetate 8:2). The organic phase was washed with water and dried over sodium sulfate, after evaporation of the solvent were obtained 4.5 g of compound I as an oil that solidify after standing. A sample was crystallized in toluene obtaining a white powder, mp117-118° C.

$H_1$NMR (CDCl$_3$, δ ppm): 1.04 (s, 3H), 1.37 (s, 3H), 1.61 (m, 12H), 1.73 (s, 3H), 2.25 (d, 1H), 2.46 (d, 1H), 3.90-4.10 (bs, 2OH), 7.25 (m, 3H), 7.80 (s, 1H), 7.92 (d, 2H), 8.00 (d, 1H).

The invention claimed is:

1. A process for the preparation of 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer 5) comprising the following steps:
  i. cumene is acylated with a compound of formula Ia, where $X_0$ is Cl or Br to obtain a compound of formula IIa and the compound of formula IIa is halogenated to obtain a compound of formula III, where $X_1$ is Cl or Br; or cumene is halogenated to obtain a compound of formula IIb and the compound of formula IIb is acylated with the compound of formula Ia to obtain the compound of formula III, according to the following scheme:

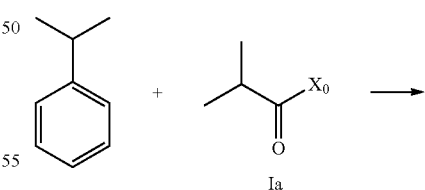

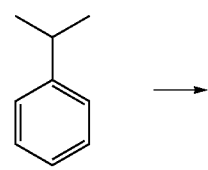

-continued

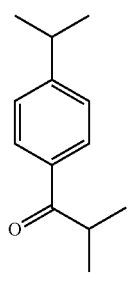

IIa

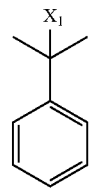

IIb

+

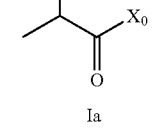

III

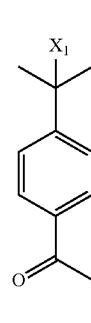

Ia ii. the compound of formula III is dehydrohalogenated with a base to obtain a compound of formula IV and the compound of formula IV is cyclized with an acid catalyst to obtain the compound of formula V, according to the following scheme:

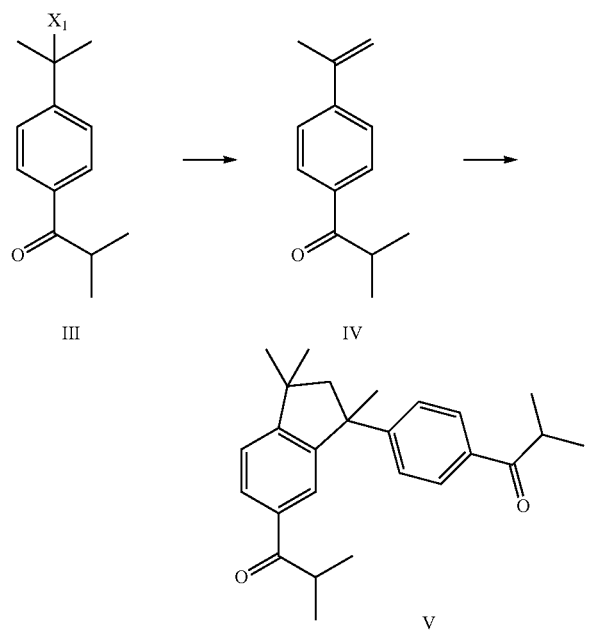

or the compound of formula III is directly cyclized with an acid catalyst to obtain the compound of formula V;

iii. the compound of formula V is halogenated to obtain the compound of formula VI

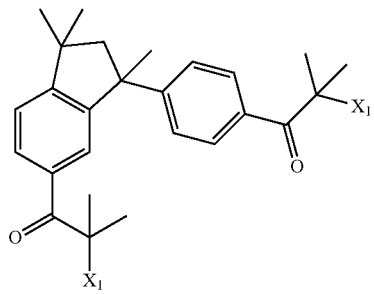

VI iv. the compound of formula VI is hydrolyzed to obtain the compound of formula VII (dimer isomer 5)

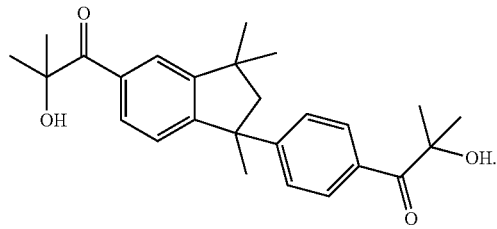

VII

2. The process according to claim 1, wherein the compound of formula Ia is isobutyryl chloride.

3. The process according to claim 1, wherein, in step i, from 1.50 to 1.10 moles of the compound of formula Ia and from 1.5 to 0.1 moles of a Lewis acid per mole of cumene are used.

4. The process according to claim 1, wherein, in step ii, the base is an alkali metal hydroxide.

5. The process according to claim 1, wherein, in step ii, the acid catalyst used in the cyclization of compound IV is a Lewis acid or an inorganic acid.

6. The process according to claim 1, wherein, in step iv, the compound of formula VI is hydrolysed by reaction with an alkali metal alkoxide and reaction with an aqueous acid.

7. The process according to claim 6, wherein the alkali metal alkoxide is sodium methylate.

8. The process according to claim 1, wherein, in step iv, the compound of formula VI is hydrolysed by reaction with an alkali metal hydroxide.

9. The process according to claim 8, wherein the alkali metal hydroxide is NaOH 30 wt % in methanol or in water.

10. The process according to claim 9, wherein the dimer isomer 5 is obtained in solid and pure form by crystallization after completing step iv.

11. The process according to claim 1, wherein the dimer isomer 5 is obtained in solid and pure form by crystallization after completing step iv.

* * * * *

UNITED STATES PATENT AND TRADEMARK OFFICE
CERTIFICATE OF CORRECTION

PATENT NO. : 10,017,435 B2
APPLICATION NO. : 15/316296
DATED : July 10, 2018
INVENTOR(S) : Gabriele Norcini et al.

It is certified that error appears in the above-identified patent and that said Letters Patent is hereby corrected as shown below:

On the Title Page

Item [73], delete "IGH Resins Italia S.R.L." and insert -- IGM Resins Italia S.R.L. --

Signed and Sealed this
Eighteenth Day of September, 2018

Andrei Iancu
*Director of the United States Patent and Trademark Office*